(12) United States Patent
Gutwein (10) Patent No.: US 6,702,837 B2
(45) Date of Patent: Mar. 9, 2004

(54) THERAPEUTIC LIGHT DEVICE (76) Inventor: Phillip Gutwein, 25 Forestgrove Cir., Brampton, Ontario (CA), L6Z 4T3

( * ) Notice: Subject to any disclaimer, the term of this patent is extended or adjusted under 35 U.S.C. 154(b) by 1 day.

(21) Appl. No.: 10/128,810

(22) Filed: Apr. 23, 2002

(65) Prior Publication Data

US 2003/0199946 A1 Oct. 23, 2003

(51) Int. Cl.[7] .................................................. A61N 5/06
(52) U.S. Cl. ............................................. 607/88; 606/9
(58) Field of Search ........................... 606/9; 607/88–91

(56) References Cited

U.S. PATENT DOCUMENTS

| 4,646,743 A | | 3/1987 | Parris | |
|---|---|---|---|---|
| 4,686,986 A | | 8/1987 | Fenyo et al. | |
| 4,930,504 A | | 6/1990 | Diamantopoulos et al. | |
| 5,304,207 A | | 4/1994 | Stromer | |
| 5,464,436 A | * | 11/1995 | Smith | 607/89 |
| 5,660,461 A | * | 8/1997 | Ignatius et al. | 362/241 |
| 5,707,137 A | * | 1/1998 | Hon | 362/183 |
| 6,084,242 A | | 7/2000 | Brown, Jr., et al. | |
| 6,187,029 B1 | * | 2/2001 | Shapiro et al. | 607/88 |
| 6,249,698 B1 | | 6/2001 | Parris | |
| 6,350,275 B1 | * | 2/2002 | Vreman et al. | 607/88 |
| 6,443,978 B1 | * | 9/2002 | Zharov | 607/91 |
| 6,471,716 B1 | * | 10/2002 | Pecukonis | 607/89 |
| 2002/0198575 A1 | * | 12/2002 | Sullivan | 607/88 |

* cited by examiner

Primary Examiner—Roy D. Gibson
Assistant Examiner—Henry M Johnson, III
(74) Attorney, Agent, or Firm—Sand & Sebolt (57) ABSTRACT

A therapeutic device for treating bodies of a human or an animal with infrared emissions from a plurality of light emitting diodes (LEDs) mounted in an applicator head. The head is connected to a handle by a flexible, position retaining neck. A battery for supplying power to the LEDs is mounted either in the handle or applicator head. A filtering lens is mounted in the applicator head for filtering out unwanted infrared emissions. The groups of LEDs emit different wavelengths and intensities to provide an effective emission pattern.

18 Claims, 8 Drawing Sheets

THERAPEUTIC LIGHT DEVICE

BACKGROUND OF THE INVENTION

1. Technical Field

The invention relates to therapeutic devices, and in particular to a device which emits infrared emissions for application to a subject to assist in the treatment of injuries.

2. Background Information

Various devices have been developed which apply radiation to an injured area of a subject, such as a human or an animal, which is believed to provide a healing effect thereon. Many of these devices use infrared emitting diodes which have infrared emissions at various wavelengths. Examples of some of these prior devices are shown in U.S. Pat. Nos. 4,646,743, 4,686,986, 4,930,504, 5,304,207, 6,084,242, and 6,249,698.

Although these devices contain various light emitting diodes (LEDs) for applying various infrared emissions onto the body of the subject at a desired location, they can be more user friendly. They require constant holding, either by the user or a second person for directing the infrared emissions onto a specific location of the subject or the device must be secured on the subject by various attachments such as tapes, bandages, wraps, etc. Furthermore, many of these devices use only one length or range of wavelengths, which although may prove satisfactory for certain treatments, are not believed to provide the same effect as a combination of diodes having various wavelength patterns. Also, these known devices emit other less desirable wavelengths which may reduce the effectiveness of the treatment.

BRIEF SUMMARY OF THE INVENTION

The therapeutic light device of the present invention provides an ergonomical device which is easily used and yet is relatively simple in construction and operation, and which provides an efficient infrared emission for directing against a specific location of a subject, which is not believed to be easily provided by the known prior therapeutic light devices.

The therapeutic light device of the present invention is a relatively lightweight hand-held device having a handle which may contain batteries for supplying the necessary energy to light emitting diodes which are mounted in an application head of the device, with the connecting neck, which extends between the handle and head, being formed of a flexible position retaining material such as the metal coils which have sufficient friction therebetween to retain the flexible neck in a preset condition. This enables the device to be placed on a subject's body with the head containing the diodes being retained at a specific location without requiring additional attachment devices such as bands, tapes, etc. since the neck can be wrapped about or over the limb of a subject to retain the device in position without requiring any external attachment devices.

A further aspect of the invention is to provide the therapeutic light device with an applicator head which contains the light emitting diodes and with a filter which contains a violet covered semi-transparent lens which filters certain wavelengths out of the infrared emissions in order to define a desired range of wavelength emissions from the diodes believed to be most effective in treating a specific area of the subject's body.

Another feature is to provide such a device in which the applicator head contains two or more groups of diodes having various wavelengths to provide effective infrared emissions for applying to a subject's body wherein one of the groups preferably has a different focal point thereby effecting the intensity of the emissions.

Still another feature of the invention is providing the applicator head with a hollow housing, which in addition to containing the light emitting diodes, contains a filtering lens, and may contain batteries for supplying the energy to the adjacent light emitting diodes.

Thus the therapeutic light device of the present invention includes a handle and an applicator head which is connected to the handle by a flexible position retaining neck with a plurality of infrared emitting diode groups mounted in the head for applying infrared radiation to a subject's body, with the energy source for energizing the diodes being mounted either in the handle or in the applicator head.

Further advantages, construction, and operation of the present invention will become more readily apparent from the following description and accompanying drawings.

BRIEF DESCRIPTION OF THE DRAWINGS

Preferred embodiments of the invention, illustrative of the best modes in which applicant contemplates applying the principles, are set forth in the following description and are shown in the drawings and are particularly and distinctly pointed out and set forth in the appended claims.

Similar numerals refer to similar parts throughout the drawings.

DETAILED DESCRIPTION OF THE INVENTION

A first embodiment of the improved therapy light device of the present invention is indicated generally at 1, and is shown in FIGS. 1–6. Device 1 includes as the main components, a handle 2, a neck 3 and an applicator head 4. As shown particularly in FIG. 2, handle 2 has a cylindrical configuration with a hollow interior 6, in which one or more batteries 7 can be inserted for supplying the electrical energy for the device with the batteries being retained in the handle by an end cap 8.

In accordance with one of the features of the invention, neck 3 is a flexible, adjustable, position retaining neck, that is, one which can be bent to various positions, and will remain in the adjusted position and has no memory attempting to return it to its previous preadjusted position. One such example is formed of helical metal coils 10, which when bent into a desired position, will retain that position due to the friction between the individual coils and since the metal per se, is not bent, but only the spacing between the coils. Other types of materials could be utilized which provides this same feature without effecting the concept of the invention.

Figure 1:
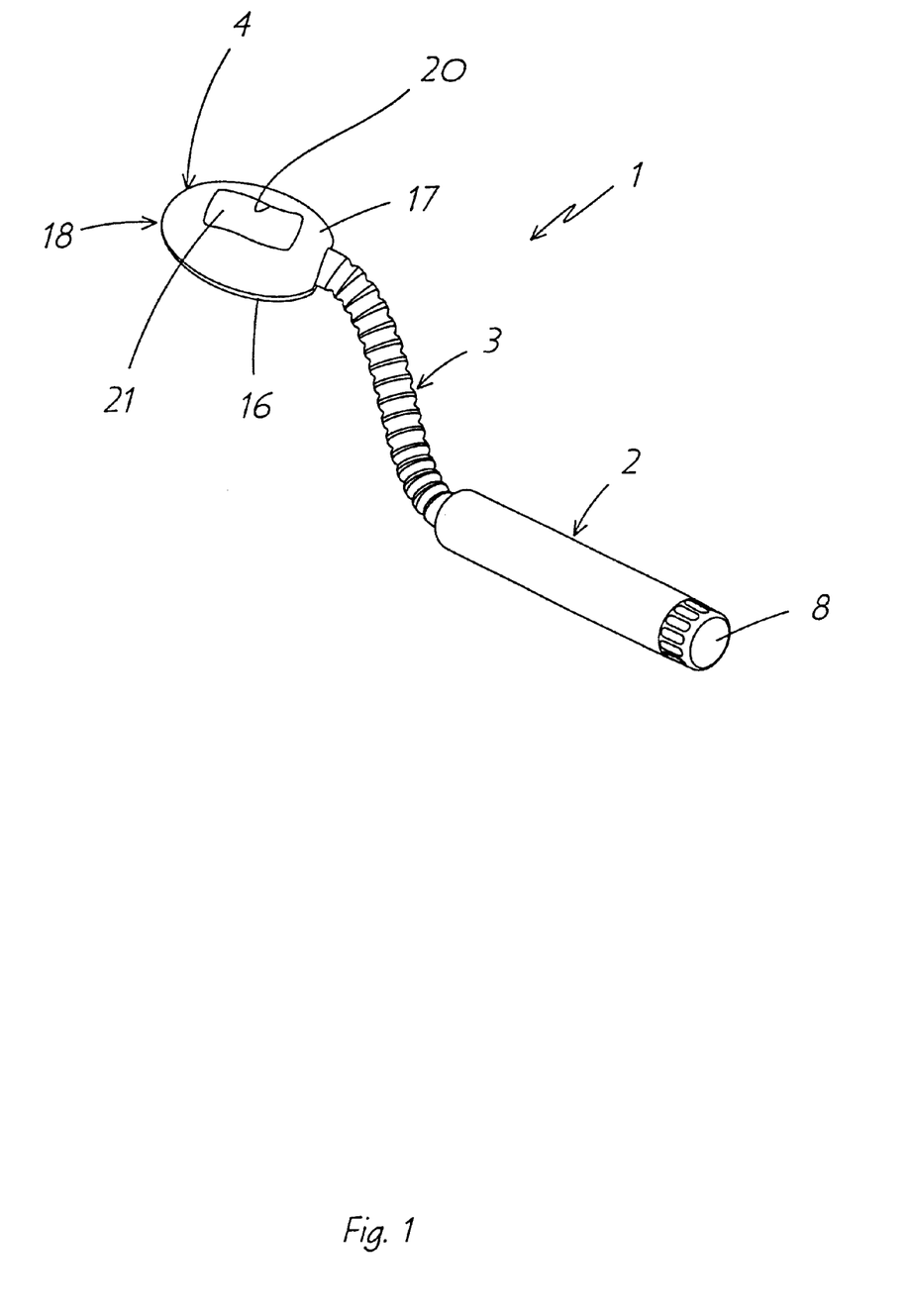
FIG. 1 is a perspective view of a first embodiment of the improved therapeutic light device.
Figure 2:
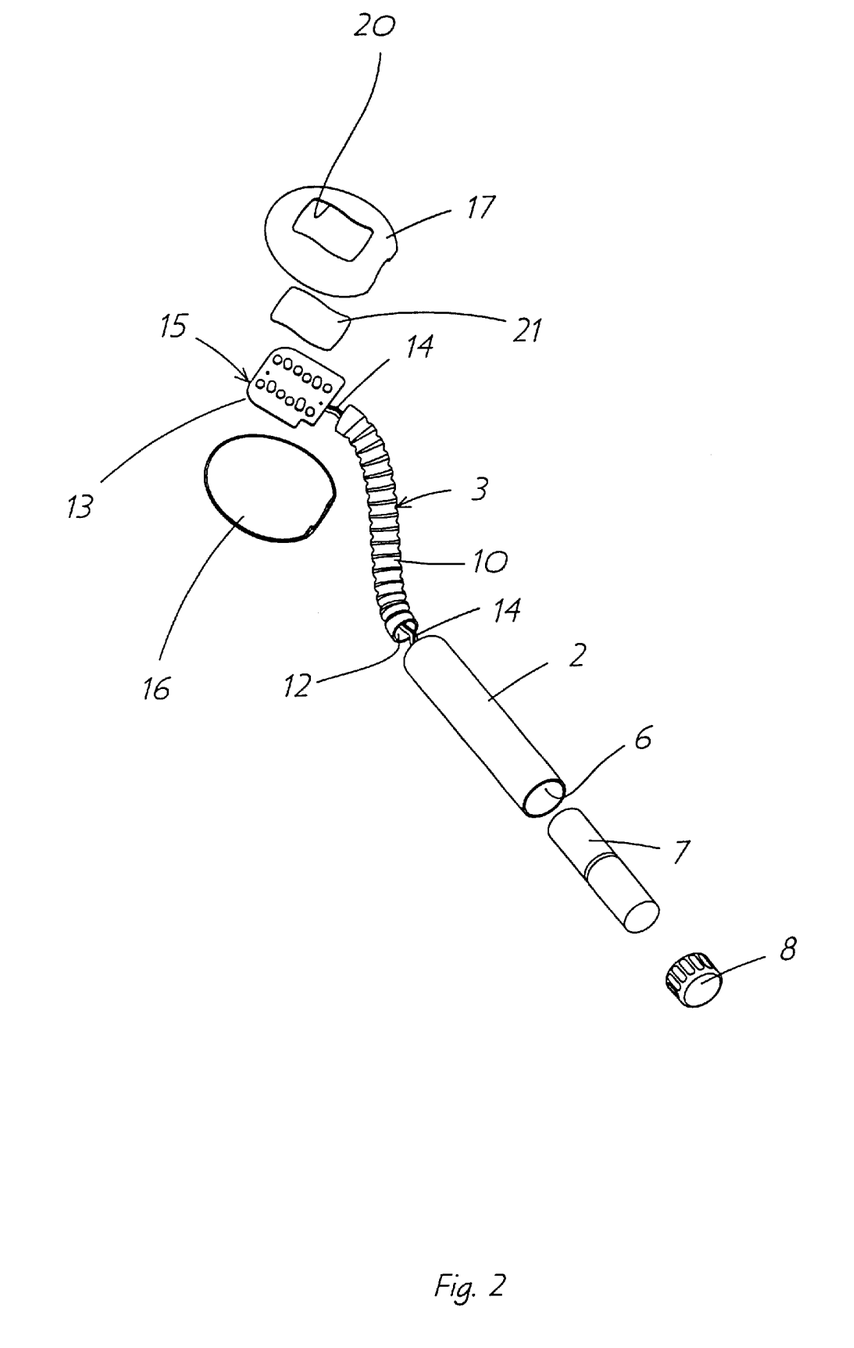
FIG. 2 is an exploded perspective view of the light device of FIG. 1.
Figure 3:
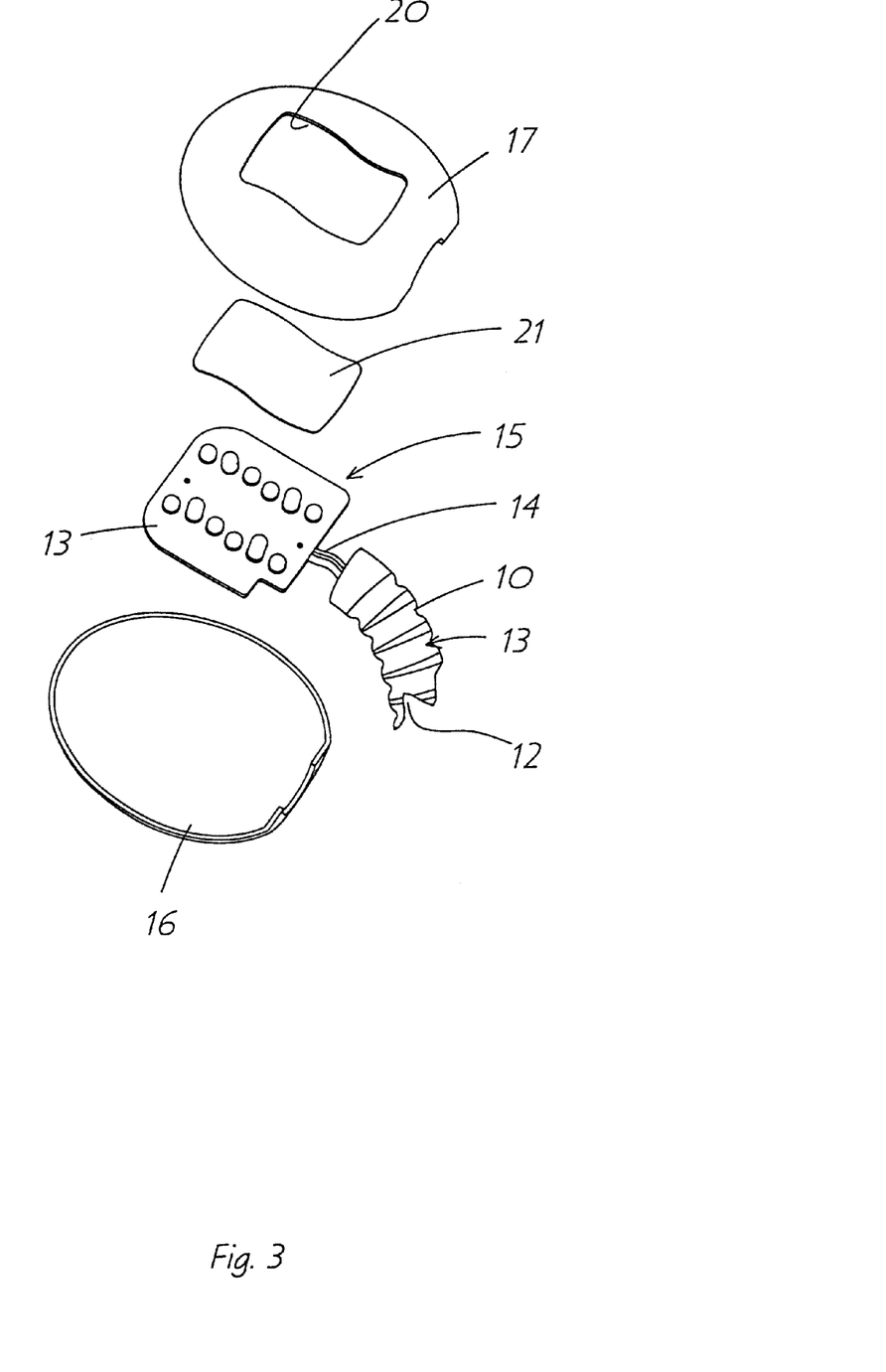
FIG. 3 is an enlarged fragmentary exploded view of the applicator head of the device of FIGS. 1 and 2.

Neck 3 also has a hollow interior 12 so that a conductor 14 can extend from handle 2 through neck interior 12 to applicator head 4 for energizing a plurality of infrared light emitting diodes (LEDs), indicated collectively at 15 which are mounted on a circuit board 13. Applicator head 4 includes a housing 18 formed by a base 16 and a cover 17, with diodes 15 being contained therein. An opening 20 is formed in cover 17 and has a lens 21 mounted therein.

Figure 4:
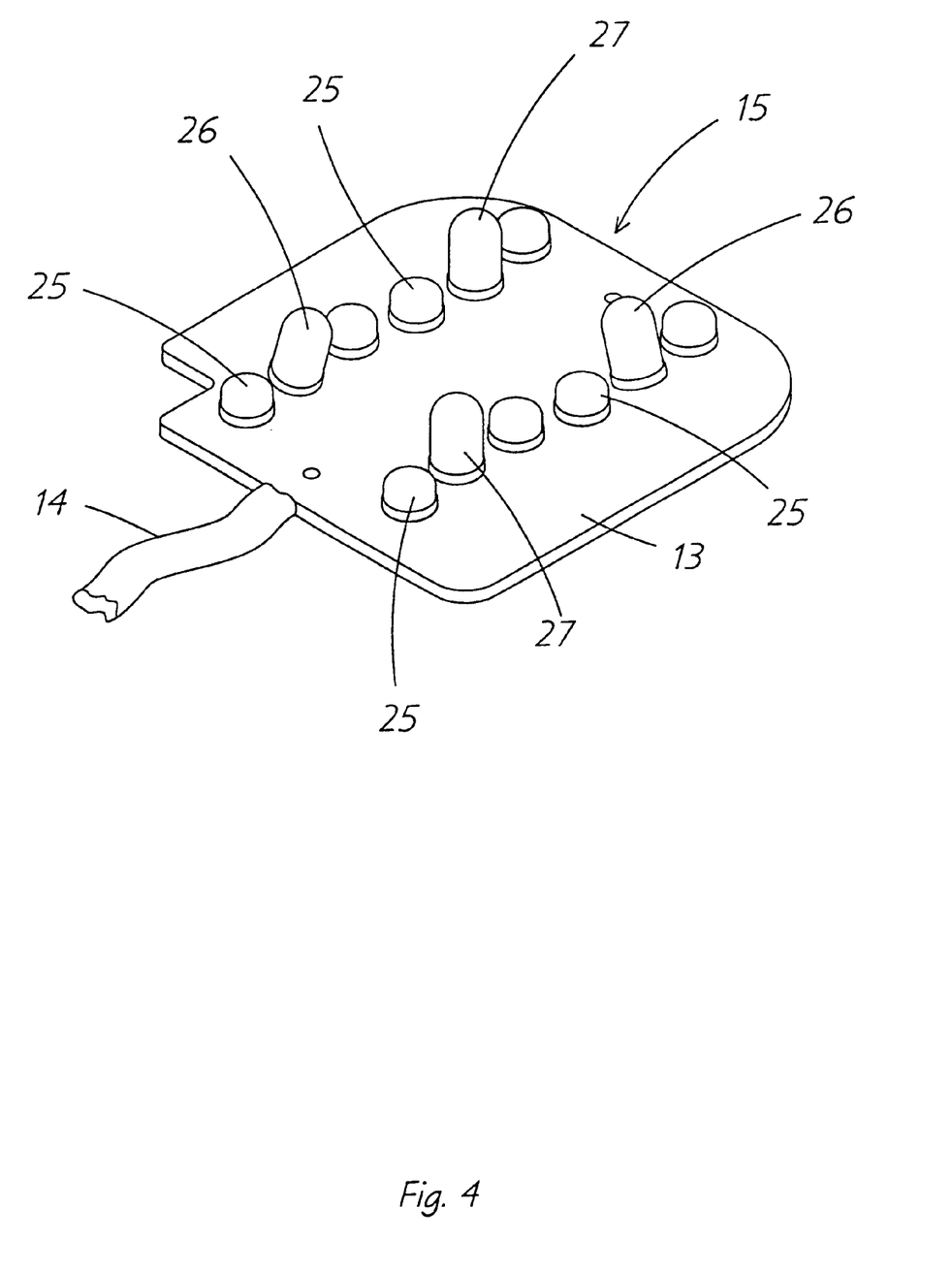
FIG. 4 is an enlarged perspective view of the light emitting diode groups removed from the applicator head.
Figure 5:
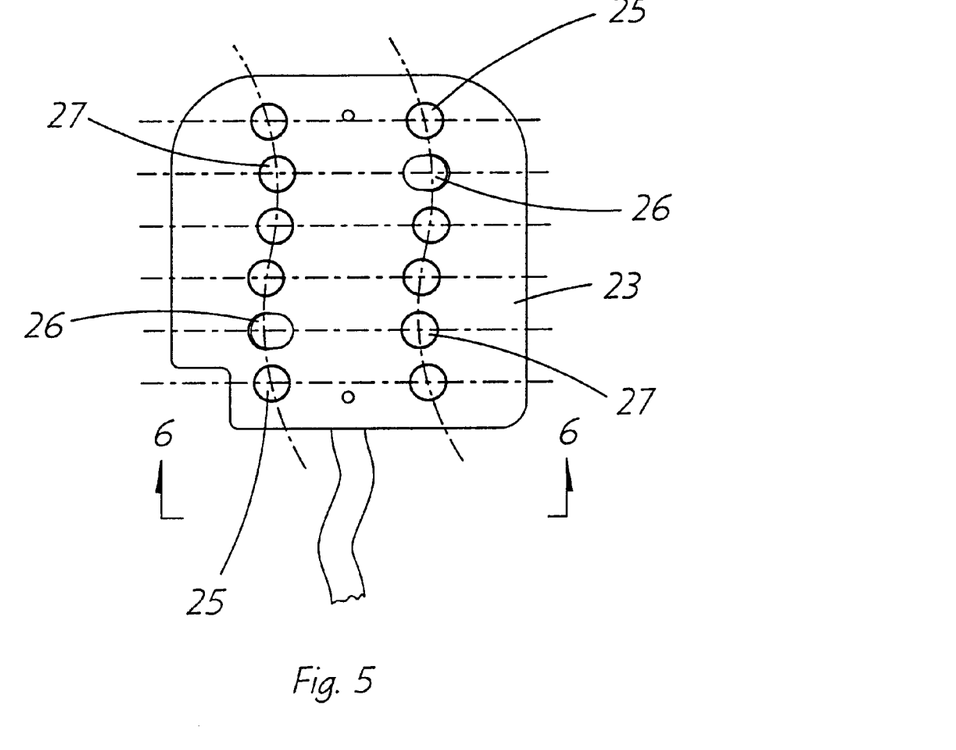
FIG. 5 is a top plan view of FIG. 4.
Figure 6:
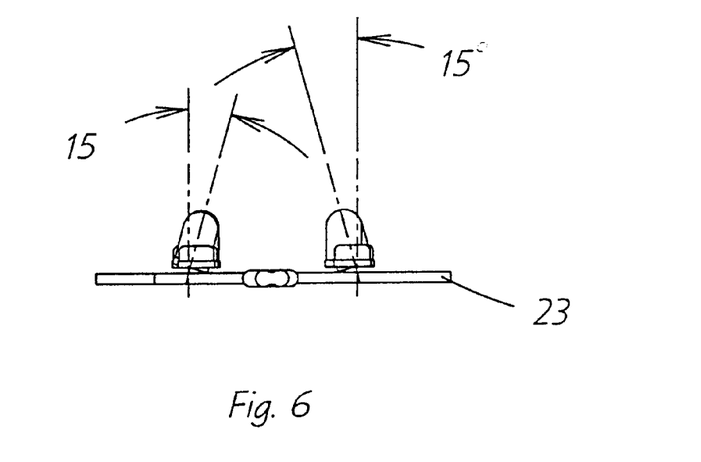
FIG. 6 is an end elevational view looking in the direction of arrows 6—6, FIG. 5.

In accordance with another feature of the invention, diodes 15, as shown in FIGS. 4–6, are mounted on circuit board 13 and preferably consist of three groups of diodes indicated as a first group of diodes 25, a second group of diodes 26, and a third group of diodes 27. In the preferred embodiment, first group consists of eight diodes 25 which have an infrared wavelength of generally between 825 nm to 925 nm, with the second group consisting of two diodes 26 having a wavelength of generally between 840 nm and 940 nm. The third group consists of two diodes 27 preferably having the same wavelength as diodes 26 in the second group, that is between 840 nm and 940 nm, but with a narrow irradiance pattern or focal length then diodes 26. In the particular embodiment shown in FIGS. 4–6, diodes 25 of group one consists of eight diodes arranged in slightly curved rows, centered about diodes 26 and 27. One type of diode 25 found satisfactory is distributed by SIEMENS® and identified as SFH 485P 2 which has a wide irradiance pattern of 90°. Diodes 26 and 27 may be of the type distributed by OPTEK® designated as OP290A and OP295A, respectively.

Diodes 26 provide a wide irradiance pattern and diodes 27 provide a narrow irradiance pattern, both having a wavelength of between 840 nm and 940 nm centered about 890 nm.

In accordance with another feature of the invention, lens 21 is a violet light polarizing filter which initiates a clockwise spin on the photons, allowing them easier access to the cell receptors which reduces treatment time. Also, the lens filters out a less desirable range of infrared and optimizes the treatment time.

Figure 7:
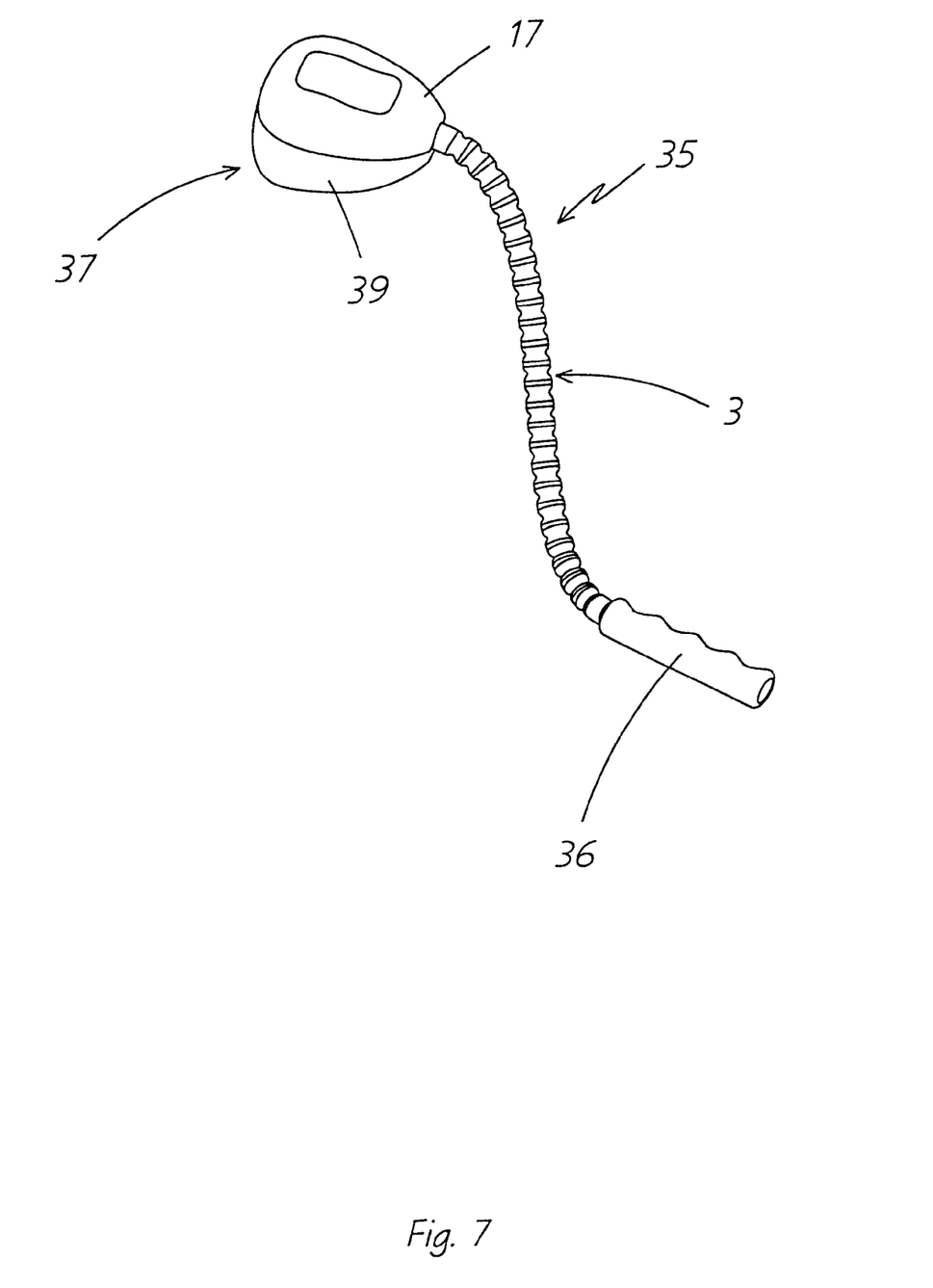
FIG. 7 is a perspective view of a second embodiment of the therapeutic light device.
Figure 8:
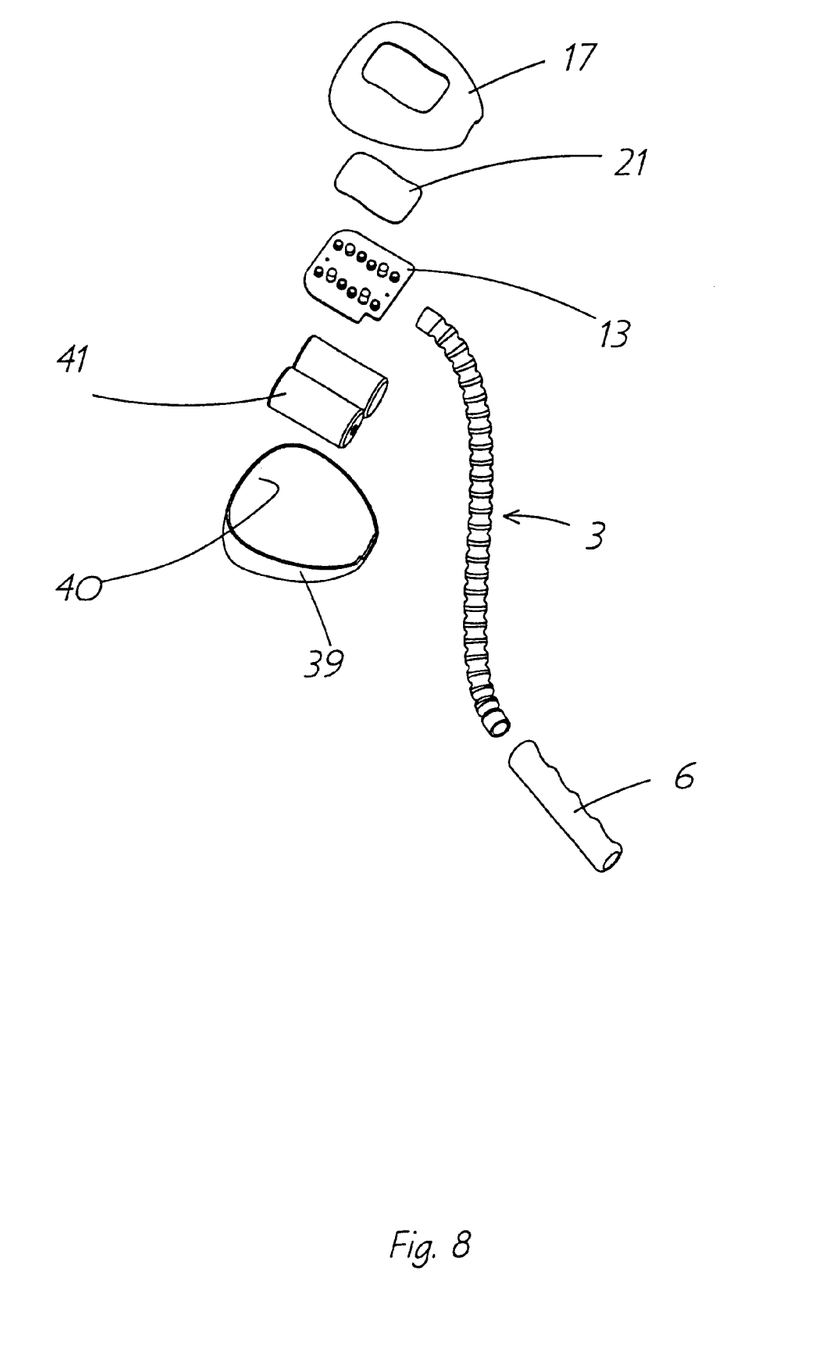
FIG. 8 is an exploded perspective view of the light device of FIG. 7.
Figure 9:
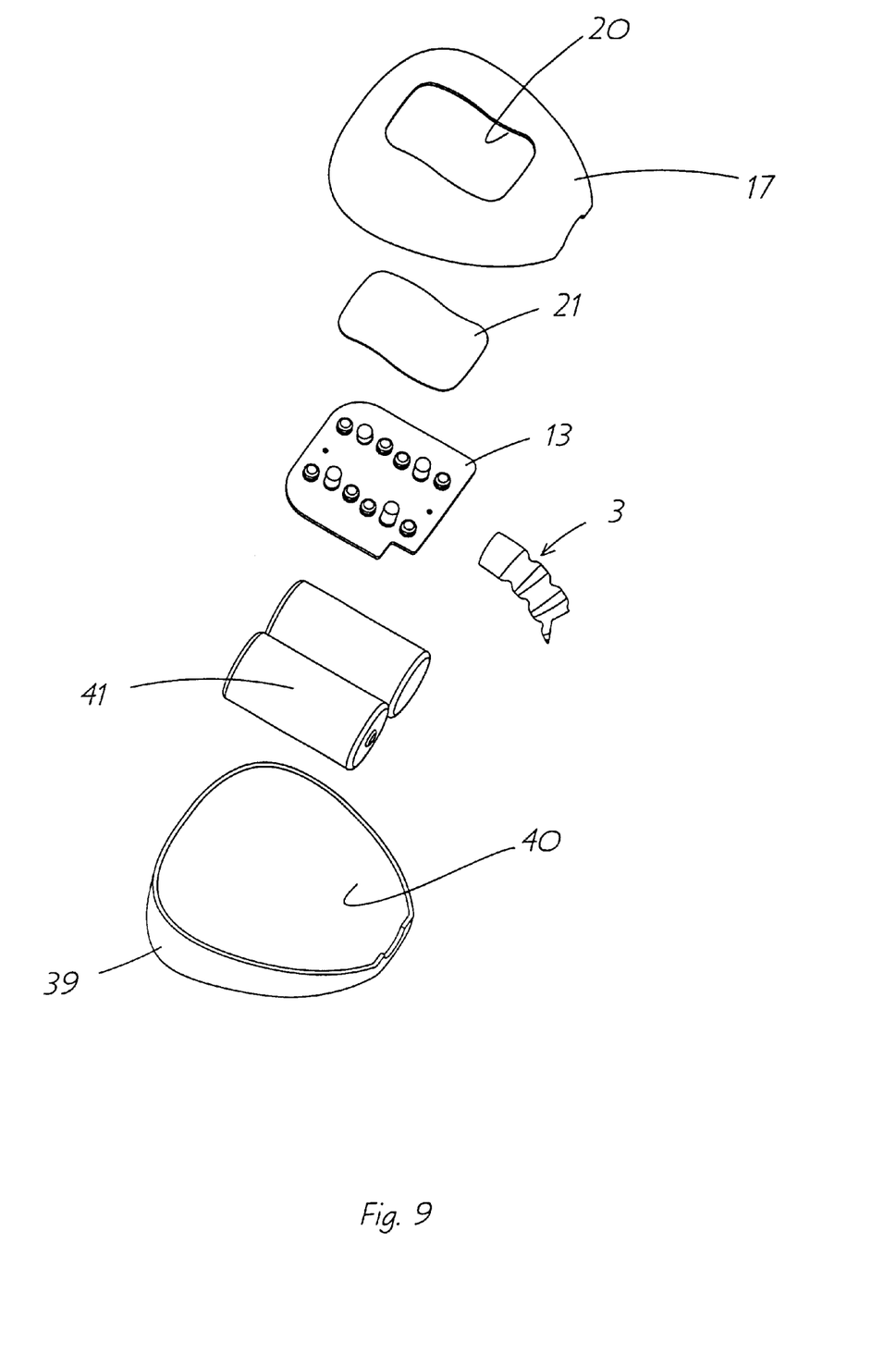
FIG. 9 is an enlarged exploded perspective view of the applicator head of the device of FIGS. 7 and 8.

A second embodiment of the improved therapeutic light device is indicated generally at 35, and is shown particularly in FIGS. 7–9. Device 35 is similar in many respects to device 1 described above, in that it includes the flexible position retaining neck 3 which extends between a handle 36 and an applicator head 37. Head 37 includes a cup-shaped base 39 having a hollow interior 40 in which is mounted batteries 41. The batteries are connected to circuit board 23 to provide the power for the various groups of diodes 25, 26 and 27 as discussed above and shown in FIGS. 4–6. The other features of device 35 are similar to those of device 1 such as cover 17 and lens 21.

In summary, the improved therapeutic light device provides an ergonomical user friendly device which enables the neck to be bent at various angles enabling the device to be placed on a user's body, such as extending over the user's shoulder with the handle being on one side of the body and the applicator head on the other, which will be retained in such a position without requiring additional attachments. Likewise, neck 3 can be wrapped about a user's limbs with the head lying adjacent the area being treated, again, without requiring any additional attachments for securing the device in position. However, if desired, the user merely can grasp the handle and apply the applicator head to the desired area being treated since the device is relatively lightweight. Also, the power source, and in particular batteries 7, can be mounted either in the handle or in the applicator head without effecting the concept of the invention.

Likewise, the unique array of readily available infrared LEDs is believed to provide an effect light pattern with enough power for treating a selected area on a subject, whether it be a human or an animal.

This array of diodes, in combination with the filtering lens, provides what is believed to be a most effective wavelength and intensities of infrared emissions directed against the area being treated. These diodes are mounted easily on a circuit board and connected to the power source by a conductor, either located in the head or extending through the hollow interior of the handle to the batteries when mounted in the handle.

While the embodiments of the invention have been described, the invention is not limited thereto.

What is claimed is:

1. A therapeutic light device comprising:
    a handle;
    an applicator head;
    an adjustable, position retaining neck extending between the handle and the applicator head;
    a plurality of infrared emitting diodes mounted in the head for applying infrared radiation to a subject's body;
    an energy source for energizing the diodes; and
    a filter in the applicator head to define a range of infrared emissions from the diodes.

2. The device defined in claim 1 wherein the energy source is a battery mounted within the handle and connected to the diodes by a conductor extending along the neck.

3. The device defined in claim 2 wherein the neck has a hollow interior; and in which the conductor extends through the hollow interior of the neck.

4. The device defined in claim 1 wherein the filter is a violet light polarizing semi-transparent lens.

5. The device defined in claim 1 wherein the diodes include at least first and second groups of diodes, each group emitting a different infrared wavelength.

6. The device defined in claim 5 wherein the first group of diodes have wavelengths of about 825 nm to 925 nm and the second group have wavelengths of about 840 nm to 940 nm.

7. The device defined in claim 6 wherein the diodes include a third group of diodes having a wavelength similar to the wavelength of the second group but with a narrower irradiance pattern.

8. The device defined in claim 1 wherein the energy source is a battery mounted in the applicator head.

9. A therapeutic light device comprising:

an applicator head;

at least first and second groups of infrared emitting diodes mounted in the head for applying infrared radiation to a subject's body, each of said groups emitting infrared radiation at different wavelengths, with certain of said diodes having different irradiance patterns than other of said diodes;

an energy source for energizing the diodes; and a filter in the applicator head to define a range of infrared emissions from the diodes.

10. The device defined in claim 9 wherein the first group of diodes have wavelengths of about 825 nm to 925 nm and the second group have wavelengths of about 840 nm to 940 nm.

11. The device defined in claim 10 wherein the diodes include a third group of diodes having a wavelength similar to the wavelength of the second group but with a narrower irradiance pattern.

12. The device defined in claim 9 including a handle and a flexible, adjustable, position retaining neck extending between the handle and applicator head.

13. A therapeutic light device comprising:

a handle;

an applicator head;

a plurality of infrared emitting diodes mounted in the head for applying infrared radiation to a subject's body;

an energy source for energizing the diodes; and a lens for initiating a clockwise spin on photons contained in infrared emissions from the diodes.

14. The device defined in claim 13 wherein a flexible, adjustable, position retaining neck extends between the head and handle.

15. The device defined in claim 13 wherein the lens is a violet light polarizing semi-transparent filter.

16. The device defined in claim 13 wherein there is at least two groups of diodes, each group providing infrared emissions of different wavelengths.

17. The device defined in claim 16 wherein the infrared emission from the diodes of one of said groups has a wavelength between 825 nm and 925 nm and from the other of said groups has a wavelength between 840 nm and 940 nm.

18. The device defined in claim 16 wherein a third group of diodes is mounted in the head and has a wavelength range similar to that of the other of said groups but with a narrower irradiance pattern.

* * * * *